United States Patent
Massey et al.

(10) Patent No.: US 6,448,091 B1
(45) Date of Patent: Sep. 10, 2002

(54) METHOD AND APPARATUS FOR IMPROVED LUMINESCENCE ASSAYS USING PARTICLE CONCENTRATION CHEMILUMINESCENCE DETECTION

(75) Inventors: Richard J. Massey, Rockville; Gary F. Blackburn, Gaithersburg; Elizabeth W. Wilkins, Germantown; Haresh P. Shah, Gaithersburg, all of MD (US)

(73) Assignee: IGEN International, Inc., Gaithersburg, MD (US)

( * ) Notice: Subject to any disclaimer, the term of this patent is extended or adjusted under 35 U.S.C. 154(b) by 0 days.

(21) Appl. No.: 08/335,183

(22) Filed: Nov. 7, 1994

Related U.S. Application Data (63) Continuation of application No. 07/728,194, filed on Jul. 10, 1991, now abandoned, which is a continuation-in-part of application No. 07/652,427, filed on Feb. 6, 1991, now abandoned, which is a continuation-in-part of application No. 07/539,389, filed on Jun. 18, 1990, now abandoned, which is a continuation of application No. 07/266,882, filed on Nov. 3, 1988, now abandoned, application No. 08/335,183, which is a continuation-in-part of application No. 07/539,389.

(51) Int. Cl.[7] .................. G01N 21/76; G01N 33/566; G01N 33/551; G01N 33/553
(52) U.S. Cl. .................. 436/501; 436/524; 436/526; 436/528; 436/172
(58) Field of Search .................. 435/7.1, 7.7, 7.72, 435/7.9, 7.91, 7.92, 25, 28, 968; 436/518, 526, 805

(56) References Cited

U.S. PATENT DOCUMENTS 4,280,815 A  *  7/1981  Oberhardt et al. .......... 436/518
4,652,533 A  *  3/1987  Jolley ........................ 422/101
4,704,255 A  *  11/1987  Jolley ........................ 422/101
4,713,324 A  *  12/1987  Fox et al. ..................... 435/4
5,196,349 A  *  3/1993  Piran et al. ................. 436/500

FOREIGN PATENT DOCUMENTS

WO           0030087      *   6/1981
WO           WO86815      *  10/1986

OTHER PUBLICATIONS

Wolf–Rogers et al, J. Imm. Meth. vol. 133, pp. 191–198 (1990), "A chemiluminescat, microparticle–membrane capture immunoassay for the detection of antibody to hepatitus B core antigen".*

* cited by examiner

Primary Examiner—Jyothsna Venkat
Assistant Examiner—Tomas Friend
(74) Attorney, Agent, or Firm—Kramer Levin Naftalis & Frankel LLP; Barry Evans, Esq.

(57) ABSTRACT

Methods and apparatus for performing a binding assay for an analyte of interest present in a sample are described. The methods include the steps of: forming a composition containing the sample, an assay-performance-substance which contains a component linked to a label compound capable of chemiluminescing when triggered, and a plurality of particles capable of specifically binding with the analyte and/or the assay-performance-substance; incubating the composition to form a complex which includes a particle and the labeled component; collecting the complex in a collection zone; introducing into the collection zone a trigger capable of triggering the label such that the label luminesces; and measuring the emitted luminescence to measure the presence of the analyte of interest in the sample.

30 Claims, 7 Drawing Sheets

METHOD AND APPARATUS FOR IMPROVED LUMINESCENCE ASSAYS USING PARTICLE CONCENTRATION CHEMILUMINESCENCE DETECTION

This application is a continuation of application Ser. No. 07/728,194, filed Jul. 10, 1991, now abandoned, is a continuation-in-part of Massey et al. application Ser. No.07/652,427 now abandoned filed Feb. 6, 1991, which is a continuation-in-part of application Ser. No. 07/539,389 now abandoned filed Jun. 18, 1990, which is a continuation of application Ser. No. 07/266,882 filed Nov. 3, 1988, now abandoned, entitled Electrochemiluminescent Assays, and this application is a continuation-in-part of copending application Ser. No. 07/539,389 now abandoned filed Jun. 18, 1990, which is a continuation of application Ser. No. 07/266,882 filed Nov. 3, 1988, now abandoned, entitled Electrochemiluminescent Assays. The subject matter of these applications is incorporated herein by reference.

FIELD OF THE INVENTION

This application relates generally to methods and apparatus for conducting binding assays, more particularly to those which measure the presence of an analyte of interest by measuring luminescence emitted by one or more labeled components of the assay system. More specifically, the invention relates to precise, reproducible, accurate homogeneous or heterogeneous specific binding assays of improved sensitivity in which the luminescent component is concentrated in the assay composition and collected before being caused to chemiluminescence.

BACKGROUND OF THE INVENTION

Numerous methods and systems have been developed for the detection and quantitation of analytes of interest in biochemical and biological substances. Methods and systems which are capable of measuring trace amounts of microorganisms, pharmaceuticals, hormones, viruses, antibodies, nucleic acids and other proteins are of great value to researchers and clinicians.

A very substantial body of art has been developed based upon the well known binding reactions, e.g., antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials. Of particular interest are labels which can be made to luminesce through photochemical, chemical, and electrochemical means. "Photoluminescence" is the process whereby a material is induced to luminesce when it absorbs electromagnetic radiation. Fluorescence and phosphorescence are types of photoluminescence. "Chemiluminescent" processes entail the creation of luminescent species by chemical transfer of energy. "Electrochemiluminescence" entails creation of luminescent species electrochemically.

Chemiluminescent assay techniques where a sample containing an analyte of interest is mixed with a reactant labeled with a chemiluminescent label have been developed. The reactive mixture is incubated and some portion of the labeled reactant binds to the analyte. After incubation, the bound and unbound fractions of the mixture are separated and the concentration of the label in either or both fractions can be determined by chemiluminescent techniques. The level of chemiluminescence determined in one or both fractions indicates the amount of analyte of interest in the biological sample.

It is desirable to carry out chemiluminescent assays without the need for a separation step during the assay procedure and to maximize the signal modulation at different concentrations of analyte so that precise and sensitive measurements can be made.

Among prior art methods for separation assays are those such as described in U.S. Pat. No. 4,141,687 and European Patent Application 0,030,087 which relate to magnetically separating particles in a conduit after which the particles are removed to a separate chamber for analysis of the label.

Among prior art methods for nonseparation assays are those which employ microparticulate matter suspended in the assay sample to bind one or more of the binding components of the assay.

U.S. Pat. No. 4,305,925 relates to the detection and determination of clinically relevant proteins and peptides by means of nephelometric and turbidimetric methods. The methods disclosed involve binding the antigen or antibody to latex particles which perform the function of light scattering or adsorption.

U.S. Pat. No. 4,480,042 relates to techniques employing particle reagents consisting of shell-core particles. The shell contains functional groups to which compounds of biological interest can be covalently bonded, and the high refractive index of the core results in high sensitivity to light scattering measurements. The technique is based upon agglutination reactions which result from the reaction of bivalent antibodies with multivalent antigens of interest to produce aggregates which can be detected and/or measured in various ways.

U.S. Pat. No. 4,419,453 likewise relates to the use of colored latex agglutination test methods useful for detecting the presence of immunochemicals such as antibodies and immunogens.

Based upon this prior art, it would not have appeared possible to use microparticulate matter in assays wherein a luminescent phenomenon is measured. One would expect that the luminescence from free chemiluminescent moieties would be absorbed, scattered, or otherwise suffer interference from the microparticulate matter.

Contrary to that expectation, U.S. application Ser. No. 266,882 (PCT published application U.S. 89/04919) teaches sensitive, specific binding assay methods based on a luminescent phenomenon wherein inert microparticulate matter is specifically bound to one of the binding reactants of the assay system. The assays may be performed in a heterogeneous (one or more separation steps) assay format and may be used most advantageously in a homogeneous (nonseparation) assay format.

U.S. 89/04919 relates to a composition for an assay based upon a binding reaction for the measurement of luminescent phenomenon, which composition includes a plurality of suspended particles having a surface capable of binding to a component of the assay mixture. In another aspect, it is directed to a system for detecting or quantitating an analyte of interest in a sample, which system is capable of conducting the assay methods using the assay compositions of the inventions. The system includes means for inducing the label compound in the assay medium to luminesce, and means for measuring the luminescence to detect the presence of the analyte of interest in the sample.

Thus, U.S. 89/04919 is directed to methods for the detection of an analyte of interest in a sample, which method includes the steps of (1) forming a composition comprising (a) a sample suspected of containing an analyte of interest, (b) an assay-performance-substance selected from the group consisting of (i) analyte of interest or analog of the analyte of interest, (ii) a binding partner of the analyte of interest or its said analog, and (iii) a reactive component capable of binding with (i) or (ii), wherein one of said substances is linked to a label compound having a chemical moiety capable of being induced to luminesce, and (c) a plurality of suspended particles capable of specifically binding with the analyte and/or a substance defined in (b)(i), (ii), or (iii); (2) incubating the composition to form a complex which includes a particle and said label compound; (3) inducing the label compound to luminesce; and (4) measuring the luminescence emitted by the composition to detect the presence of the analyte of interest in the sample. Those same methods may be used to quantify the amount of analyte in a sample by comparing the luminescence of the assay composition to the luminescence of a composition containing a known amount of analyte.

Analogs of the analyte of interest, which may be natural or synthetic, are compounds which have binding properties comparable to the analyte, but include compounds of higher or lower binding capability as well. Binding partners suitable for use in the present invention are well-known. Examples are antibodies, enzymes, nucleic acids, lectins, cofactors and receptors. The reactive components capable of binding with the analyte or its analog and/or with a binding partner thereof may be a second antibody or a protein such as Protein A or Protein G or may be avidin or biotin or another component known in the art to enter into binding reactions.

Advantageously, the luminescence arises from electrochemiluminescence (ECL) induced by exposing the label compound, whether bound or unbound to specific binding partners, to a voltametric working electrode. The ECL reactive mixture is controllably triggered to emit light by a voltage impressed on the working electrode at a particular time and in a particular manner to generate light. Although the emission of visible light is an advantageous feature the composition or system may emit other types of electromagnetic radiation, such as infrared or ultraviolet light, X-rays, microwaves, etc. Use of the terms "electrochemiluminescence," "electrochemiluminescent," "luminescence," "luminescent," and "luminesce" includes the emission of light and other forms of electromagnetic radiation.

The methods taught in U.S. 89/04919 permit the detection and quantitation of extremely small quantities of analytes in a variety of assays performed in research and clinical settings. The demands of researchers and clinicians makes it imperative, however, to lower the detection limits of assays performed by these methods to increase the sensitivities of those assays and to increase the speed at which they can be performed.

Various methods are known in the art for increasing the signal from labeled species by concentrating them before subjecting them to a measurement step. In U.S. Pat. No. 4,652,333, for example, particles labeled with fluorescent, phosphorescent or atomic fluorescent labels are concentrated by microfiltration before a measurement step is performed.

It is also known in the art to concentrate labeled immunochemical species prior to a measurement step, by, e.g., drawing magnetically responsive labeled particles to the surface of a measurement vessel. In U.S. Pat. Nos. 4,731, 337, 4,777,145, and 4,115,535, for example, such particles are drawn to the vessel wall and then are irradiated to excite a fluorophoric emission of light.

In U.S. Pat. No. 4,945,045, particles are concentrated on a magnetic electrode. An electrochemical reaction takes place at the electrode facilitated by a labeled chemical mediator. The immunochemical binding reaction alters the efficiency of the mediator resulting in a modulated signal when binding takes place.

OBJECTS OF THE INVENTION

It is therefore a primary object of this invention to provide homogeneous (non-separation) and heterogeneous (separation) methods, reagents and apparatus, for the conduct of binding assays.

It is a further object of this invention to provide non-separation, specific binding assays, reagents and apparatus, based upon the measurement of chemiluminescence emitted from an assay composition containing microparticulate matter.

It is a further and related object to provide such assays, reagents and apparatus having improved sensitivity, faster assay time, greater sensitivity, lower detection limits and greater precision than has heretofore been achieved.

DESCRIPTION OF THE INVENTION

Definition of Terms

Chemiluminescence is defined as a luminescence reaction in which the energy responsible for generating the high-energy excited state of a molecule is derived from an energetic chemical reaction. A chemiluminescent reaction thus involves the direct conversion of chemical energy to electromagnetic radiation (ultraviolet, visible, or infrared radiation). Luminescence occurs when the excited-state molecule returns to its ground-state energy level, emitting a photon having a particular wavelength which is characteristic of the molecule and the energy of its excited state relative to its ground-state.

Energy is generated by many chemical reactions; such reactions are called exothermic reactions. In most cases the energy appears as heat and induces vibrational, rotational, and translational energy in the molecule. In a chemiluminescence reaction at least part of this energy is channeled into the formation in the high-energy excited state. This generally requires a highly energetic and rapid reaction of two molecules, one of which is capable of luminescence emission:

$$A+B \rightarrow C^*+D$$

$$C^* \rightarrow C+hV$$

The quantity hV represents a photon of electromagnetic radiation. h is Planck's constant and hV is the frequency of the emitted light.

In some chemiluminescent reactions the electronic energy of the excited-state molecule $C^*$ is transferred to another molecule, $$C^*+E \rightarrow C+E^*$$

which then decays to its ground-state by emitting a photon of electromagnetic radiation, $$E^* \rightarrow E+hV$$

Specific binding assays, e.g. immunoassays, using chemiluminescent detection use one of the reactants as a label attached to one of the binding partners. In such assays, the reactants are generally called the label and the trigger and react according to the equation:

Examples of chemiluminescent labels which have been used in specific binding assays include acridinium esters, luminol, isoluminol, oxalate esters, dioxetanes, and luciferin. In many cases, the trigger molecule is an oxidant such as hydrogen peroxide which is capable of oxidizing the label in a highly energetic reaction which is capable of generating the excited state of the label.

Enhancer molecules are sometimes used in chemiluminescent reactions as a means of increasing the efficiency of the chemiluminescence process. Such molecules generally slow the reaction rate of the reaction and increase the quantum yield of the light emission.

Chemiluminescent binding assays have also been demonstrated in which an enzyme is used as the label. In these cases, the enzyme catalyzes the chemiluminescent reaction in the presence of a trigger solution. An example is the use of the enzyme horseradish peroxidase to catalyze the chemiluminescent reaction of luminol in the presence of hydrogen peroxide and hydroxide ion.

The term "chemiluminescent moiety," "label," "label compound," and "label substance," are used interchangeably. It is within the scope of the invention for the species termed "chemiluminescent moiety," "label compound," "label substance" and "label" to be linked to molecules such as an analyte or an analog thereof, a binding partner of the analyte or an analog thereof, and further binding partners of such aforementioned binding partner, or a reactive component capable of binding with the analyte, an analog thereof or a binding partner as mentioned above. The above-mentioned species can also be linked to a combination of one or more binding partners and/or one or more reactive components. Additionally, the aforementioned species can also be linked to an analyte or its analog bound to a binding partner, a reactive component, or a combination of one or more binding partners and/or one or more reactive components. It is also within the scope of the invention for a plurality of the aforementioned species to be bound directly, or through other molecules as discussed above, to an analyte or its analog. For purposes of brevity, these ligands are referred to as an assay-performance-substance.

The terms detection and quantitation are referred to as "measurement", it being understood that quantitation may require preparation of reference compositions and calibrations.

The terms collection and concentration of complex may be used interchangeably to describe the concentration of complex within the assay composition and the collection of complex at, e.g., a surface of a flow cell.

Advantageously, the luminescence arises from chemiluminescence induced by exposing the label compound, whether bound or unbound to specific binding partners, to a trigger capable of triggering said label such that the label luminesces. Preferably, the trigger is an oxidant capable of oxidizing said label such that the label is oxidized and luminesces. The chemiluminescent reactive mixture is controllably triggered to emit light at a particular time and in a particular manner to generate light. Although the emission of visible light is an advantageous feature, the composition or system may emit other types of electromagnetic radiation, such as infrared or ultraviolet light, X-rays, microwaves, etc. Use of the terms "chemiluminescence" and "chemiluminescent" includes the emission of light and other forms of electromagnetic radiation.

BRIEF DESCRIPTION OF THE EMBODIMENT

In its broadest embodiment, the invention is in a method for performing a binding assay for an analyte of interest present in a sample. The steps include:
 (a) forming a composition containing
  (i) said sample
  (ii) an assay-performance-substance which contains a component linked to a label compound capable of chemiluminescing when triggered, and
  (iii) a plurality of particles capable of specifically binding with the analyte and/or said assay-performance-substance;
 (b) incubating said composition to form a complex which includes a particle and said labeled component;
 (c) collecting said complex in a collection zone;
 (d) introducing into said collection zone a trigger capable of triggering said label such that said label luminesces; and
 (e) measuring the emitted luminescence to measure the presence of the analyte of interest in the sample.

Preferably, the trigger is an oxidant capable of oxidizing the label such that the label is oxidized and chemiluminesces. Also preferably, the particles are magnetically responsive and the complex is magnetically collected in the collection zone.

In another embodiment, the assay-performance-substance or the particles further contain an enzyme for converting a precursor to an oxidant capable of oxidizing the label, and the trigger is the precursor.

While the invention is carried out by collecting the complex in a measurement zone, i.e., on a surface at which it can be caused to luminesce, the invention also embraces methods wherein the complex is collected in a measurement zone and thereafter means are brought to that zone or other steps taken to induce and measure luminescence.

The collection of the complex may be carried out by several different methods, including gravity settling, filtration, centrifugation and magnetic attraction of magnetically responsive particles which form part of the complex. The several embodiments are described in further detail below.

While batch assays can be performed, continuous or semi-continuous assays can be performed in flow cells. In a flow cell, the solid-phase remains in the measurement cell while the solution flows through and exits the cell. If the solid-phase (e.g., particles) are more dense than water, i.e., have a density greater than that of water, (more than 1.0 g/mL) the force of gravity upon the particles causes them to fall to the bottom of the cell. The cell can be constructed such that the particles settle to the bottom as the fluid flows through the cell or the cell can be constructed such that the majority of the sample is contained in the cell in a columnar compartment above the collection zone. Sufficient dwell time in the cell must be provided to permit the particles to settle in the collection zone before inducing chemiluminescence.

In another embodiment of the invention, the assay composition containing suspended particles having a density greater than the balance of the assay composition may be subjected to centrifugation in order to remove the particles to a measurement zone where they are subsequently brought into contact with, e.g., a trigger to induce chemiluminescence.

In this embodiment, the measurement cell is provided with means to rapidly rotate the sample and sample enclosure. Centrifugal force causes the particles in the sample to move outward from the axis of rotation of the sample enclosure and to collect on the outer surface of the sample enclosure.

In a third embodiment, the particles may be removed by filtration from the assay composition. In this embodiment the particles need not have a density greater than the balance of the assay composition. The invention, the particles are separated from the solution and concentrated by drawing the solution through a filter, e.g. pumping and collecting the particles on the surface of the filter.

In a preferred embodiment, the suspended particles are magnetically responsive, e.g. they may be paramagnetic or ferromagnetic, and are collected in a measurement zone by imposition of a magnetic field on the particles. The measurement cell is equipped with a magnet. The magnetic field of the magnet applies a force on the particles as they reside in a batch cell or as they flow through a flow cell, causing them to separate from the bulk of the solution onto the surface of the cell which is in closest proximity to the magnet.

Several different heterogeneous and homogeneous formats for binding assays can be implemented using the methods described above to collect and concentrate the complex. In a heterogeneous binding assay the complex is separated from the composition before measuring luminescence from the label. In homogeneous assays, no separation of the bound (to the solid phase) and unbound labeled reagents is made.

In a homogeneous assay, when the complex is concentrated in a collection zone, the measured signal from the label is much greater than it would be in the absence of a concentration step. The signal from the uncomplexed labeled reagents, in contrast, is not changed. Hence, despite the presence of the uncomplexed labeled reagents in the measurement cell, the signal from the collected complex is stronger than in an assay without collection of complex. The detection limit for the binding assay is, much improved as a result of the collection procedure.

In a preferred embodiment of the invention, an in-situ separation step is included in the homogeneous binding assay procedure. After the assay composition, i.e., sample, assay performance substance and particles have been pumped into the measurement cell and the complex collected in a collection zone, a second fluid is pumped through the cell which is free of label or labeled reagents, thereby performing an in-situ wash or separation of the complex from unbound components of the assay composition. This assay procedure is technically a heterogeneous binding assay. However, the ability to perform the separation inside the measurement cell is advantageous in that it does not require additional separation apparatus and the procedure is generally much faster than external separation methods.

Heterogeneous binding assays are conducted using the invention by mixing the components of the assay composition and allowing them to react for a predetermined length of time. The assay composition is then subjected to a separation step wherein the solution is separated from the particles. Chemiluminescence is then measured from either the complex or the solution. Measuring the chemiluminescence from the complex after a concentration step permits measurement of analyte with better accuracy and with a lower detection limit than is possible without concentration.

DETAILED DESCRIPTION OF THE INVENTION

The invention, as well as other objects and features thereof, will be understood more clearly and fully from the following description of certain preferred embodiments.

The invention is broadly applicable to analytes of interest which are capable of entering into binding reactions. These reactions include, e.g., antigen-antibody, ligand receptor, DNA and RNA interactions, and other known reactions. The invention relates to different methods and assays for qualitatively and quantitatively detecting the presence of such analytes of interest in a multicomponent sample.
The Samples The sample which may contain the analyte of interest, which may be in solid, emulsion, suspension, liquid, or gas form, may be derived from, for example, cells and cell-derived products, water, food, blood, serum, hair, sweat, urine, feces, tissue, saliva, oils, organic solvents or air. The sample may further comprise, for example, water, acetonitrile, dimethyl sulfoxide, dimethyl formamide, n-methyl-pyrrolidone or alcohols or mixtures thereof.
The Analytes Typical analytes of interest are a whole cell or surface antigen, subcellular particle, virus, prion, viroid, antibody, antigen, hapten, fatty acid, nucleic acid, protein, lipoprotein, polysaccharide, lipopolysaccharide, glycoprotein, peptide, polypeptide, cellular metabolite, hormone, pharmacological agent, synthetic organic molecule, organometallic molecule, tranquilizer, barbiturate, alkaloid, steroid, vitamin, amino acid, sugar, lectin, recombinant or derived protein, biotin, avidin, streptavidin, or inorganic molecule present in the sample. Typically, the analyte of interest is present at a concentration of $10^{-3}$ molar or less, for example, as low as $10^{-12}$ molar or lower.
Assay-Performance-Substance The assay-performance-substance which is combined with the sample containing the analyte of interest contains at least one substance selected from the group consisting of (i) added analyte of interest or its analog, as defined above, (ii) a binding partner of the analyte of interest or its said analog, and (iii) a reactive component, as defined above, capable of binding with (i) or (ii), wherein one of said substances is linked to a compound or moiety, e.g. a chemiluminescent moiety capable of being induced to luminesce. The labeled substance may be a whole cell or surface antigen, a subcellular particle, virus, prion, viroid, antibody, antigen, hapten, lipid, fatty acid, nucleic acid, polysaccharide, protein, lipoprotein, lipopolysaccharide, glycoprotein, peptide, polypeptide, cellular metabolite, hormone, pharmacological agent, tranquilizer, barbiturate, alkaloid, steroid, vitamin, amino acid, sugar, nonbiological polymer (preferably soluble), lectin, recombinant or derived protein, synthetic organic molecule, organometallic molecule, inorganic molecule, biotin, avidin or streptavidin. In one embodiment, the reagent is a chemiluminescent moiety conjugated to an antibody, antigen, nucleic acid, hapten, small nucleotide sequence, oligomer, ligand, enzyme, or biotin, avidin, streptavidin, Protein A, Protein G, or complexes thereof, or other secondary binding partner capable of binding to a primary binding partner through protein interactions.

Analogs of the analyte of interest, which can be natural or synthetic, are typically compounds which have binding properties comparable to the analyte, but can also be compounds of higher or lower binding capability. The reactive components capable of binding with the analyte or its analog, and/or with a binding partner thereof, and through which the chemiluminescent moiety can be linked to the analyte, is suitably a second antibody or a protein such as Protein A or Protein G, or avidin or biotin or another component known in the art to enter into binding reactions.

The function of the chemiluminescent moieties is to emit electromagnetic radiation as a result of introduction into the reaction system of a trigger, particularly an oxidant. In order to do this, they must be capable of being stimulated to an excited energy state and also capable of emitting electromagnetic radiation, such as a photon of light, upon descending from that excited state.

The amount of chemiluminescent moiety incorporated in accordance with the invention will vary from system to system. Generally, the amount of such moiety utilized is that amount which is effective to result in the emission of a detectable, and if desired, quantitatable, emission of electromagnetic energy, from the aforementioned composition or system. The detection and/or quantitation of an analyte of interest is typically made from a comparison of the luminescence from a sample containing an analyte of interest and a chemiluminescent moiety to the luminescence emitted by a calibration standard developed with known amounts of the analyte of interest and chemiluminescent moiety. This assumes a homogeneous format. In the heterogeneous mode, a separation as discussed previously is carried out prior to chemiluminescent analysis.

As can be appreciated by one of ordinary skill in the art, the identity and amount of the chemiluminescent moiety will vary from one system to another, depending upon prevailing conditions. The appropriate chemiluminescent moiety, and sufficient amount thereof to obtain the desired result, can be determined empirically by those of ordinary skill in the art, once equipped with the teachings herein, without undue experimentation.

The Particles

The particles advantageously comprise microparticulate matter having a diameter of 0.05 um to 200 um, preferably 0.1 um to 100 um, most preferably 0.5 um to 10 um, and a surface component capable of binding to the analyte and/or one or more of the other substances defined in subparagraphs (a)(i), (a)(ii), or (a)(iii) above. For example, the microparticulate matter may be crosslinked starch, dextrans, cellulose, proteins, organic polymers, styrene copolymer such as styrene/butadiene copolymer, acrylonitrile/butadiene/ styrene copolymer, vinylacetyl acrylate copolymer, or vinyl chloride/acrylate copolymer, inert inorganic particles, chromium dioxide, oxides of iron, silica, silica mixtures, and proteinaceous matter, or mixtures thereof. Desirably, the particles are suspended in the chemiluminescent system.

Apparatus for Measuring Chemiluminescence

Figure 1:
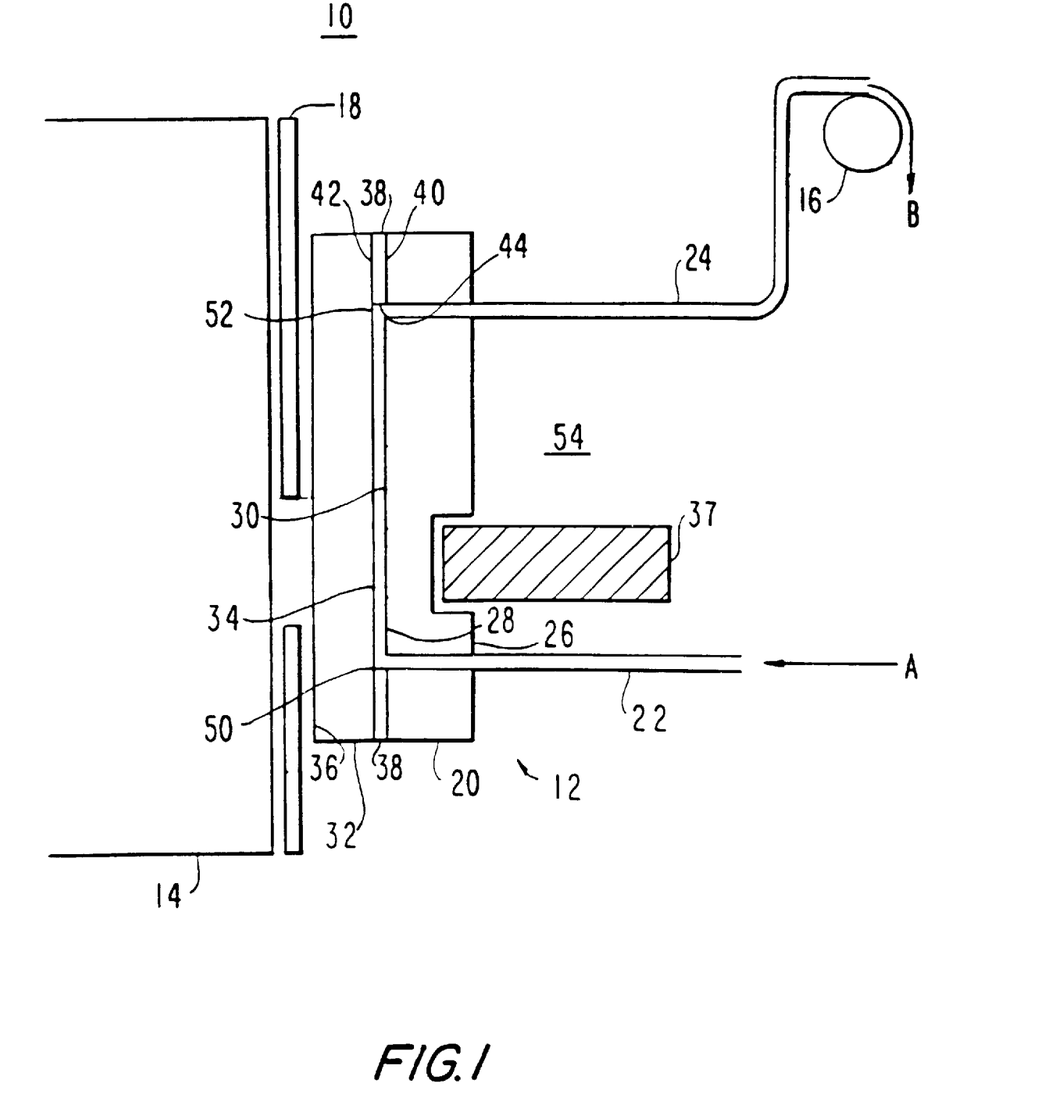
FIG. 1 is a schematic drawing of a cell including a permanent magnet for performing the microparticulate-based nonseparation and separation assays of the invention.

An apparatus for carrying out the assays of the invention is described in FIG. 1. FIG. 1 discloses an advantageous chemiluminescent apparatus, but the methods of the present invention are not limited to application in apparatus 10, but rather may be employed in other types of chemiluminescent apparatus which include a means for collecting a labeled component. While the methods of the invention can be carried out in a static or flow-through mode, apparatus 10 includes a flow-through cell, which provides distinct advantages for many types of samples including binding assay samples. Further details of apparatus for carrying out the chemiluminescent assays of the invention are disclosed in commonly assigned published PCT applications U.S. 89/04854 and U.S. 90/01370.

Apparatus 10 includes a measurement cell 12, a light detection/measurement device 14, which may advantageously be a photomultiplier tube (PMT), photodiode, charge coupled device, photographic film or emulsion or the like, and a pump 16, which is advantageously a peristaltic pump, to provide for fluid transport to, through and from cell 12. Alternatively, a positive displacement pump may be used. A shutter mechanism 18 is provided between cell 12 and PMT 14 and is controllably operated to open only so far as to expose PMT 14 to cell 12 during chemiluminescent measurement periods. The shutter mechanism may be closed, for example, during maintenance. Also included in apparatus but not illustrated in FIG. 1 is a lightproof housing intended to mount the various components therein and to shield PMT 14 from any external light during the chemiluminescent measurements.

Cell 12 itself includes a first mounting block 20 through which passes an inlet tube 22 and an outlet tube 24, which may be advantageously constructed of Plexiglas. Mounting block 20 has a first, outer surface 26 and a second, inner surface 28 defining one side of a sample-holding volume 30 of cell 12 in which cell 12 holds the cleaning and/or conditioning and/or measurement solutions during corresponding operations of apparatus 10. Inlet and outlet tubes 22, 24 pass through mounting block 20 from outer surface 26 to inner surface 28 and open into sample-holding volume 30. A second mounting block 32 is advantageously constructed of a material which is substantially transparent at the wavelength of chemiluminescent light emitted by the chemiluminescent moiety. Mounting block 32 is therefore advantageously formed of glass, plastic, quartz or the like and has a first, outer surface 34 and a second, inner surface 36. Second mounting block 32 is separated from first mounting block 20 by an annular spacer 38, advantageously constructed of Teflon or other non-contaminable material. Thus, outer surface 34 of mounting block 30 defines the second side of the sample-holding volume 30. Spacer 38 has an outer portion 40 and a central aperture 42 whose inner edge 44 defines the side wall of sample-holding volume 30. Outer portion 40 seals the inner surface 28 of first mounting block 20 to outer surface 34 of second mounting block 32 to prevent any solution from passing out from sample-holding volume 30 between the two surfaces 28, 34.

Inlet tube 22 intersects sample-holding volume 30 at a first end 50 thereof adjacent to spacer 38 and outlet tube 24 intersects sample-holding volume 30 at a second end 52 thereof, adjacent spacer 38. The combination of inlet tube 22, sample-holding volume 30 and outlet tube 24 thereby provides a continuous flow path for the narrow, substantially laminar flow of a solution to, through and from cell 12.

Pump 16 is advantageously positioned at outlet tube 24 to "pull" solution from a sample volume in the direction of arrow A into inlet tube 22. The solution will flow through inlet tube 22, sample-holding volume 30 and outlet tube 24 and out in the direction of arrow B. Alternatively, pump 16 may be positioned at inlet tube 22 to "push" the solution through apparatus 10. Advantageously, this same flow path through inlet tube 22, sample-holding volume 30 and outlet tube 24 is used for all solutions and fluids which pass through cell 12, whereby each fluid performs a hydrodynamic cleaning action in forcing the previous fluid out of cell 12. Pump 16 may be controlled to suspend its operation to hold a particular solution in cell 12 for any period of time.

The invention is also directed to reagent compositions. Broadly, the reagent compositions may be any one of the components of the assay systems of the invention, i.e., (a) electrolyte, (b) label compound containing a chemiluminescent moiety, (c) particles, including magnetically responsive particles, (d) analyte of interest or an analog of the analyte of interest, (e) a binding partner of the analyte of interest or of its analog, (f) a reactive component capable of reacting with (d) or (e), (g) a trigger precursor molecule, or (h) a chemiluminescence-reaction enhancer. The reagents may be combined with one another for convenience of use, i.e., two component, three component, and higher multiple component mixtures may be prepared, provided that the components are not reactive with one another during storage so as to impair their function in the intended assay. Desirably, the reagents are two-component or multicomponent mixtures which contain particles as well as one or more other components.

The invention is also directed to kits. The kits may include vessels containing one or more of the components (a) to (h) recited above or the kits may contain vessels containing one or more reagent compositions as described above comprising mixtures of those components, all for use in the assay methods and systems of the invention.

DESCRIPTION OF THE PREFERRED EMBODIMENT

While a wide range of particles can be employed in the particle-based assays of the invention, generally the particles have a density of from 1.0 to 5.0 g/mL and preferably have a density of from 1.1 to 2 g/mL. Choice of the optimum density is within the skill of the art, the rate of settling in gravity-driven assays being a trade-off between the speed of the assay and the desire to create a uniform layer of complex in the collection zone.

Particles having a wide range of mean diameters can also be employed. Particles having a mean diameter of from 0.001 to 100 $\mu$m can be used and preferably the particles have a mean diameter of from 0.01 to 10 $\mu$m.

Wide ranges of concentration of particles in the assay composition can also be employed. For example, the concentration can range from 1 to 10,000 $\mu$g/mL to preferably from 5 to 1000 $\mu$g/mL. Desirably, the density of the particles, their size and their concentration is selected such that the particles settle at a rate of at least 0.5 mm/min and preferably at a faster rate.

In the filtration mode of performing the invention, the filtration means desirably has a pore size, measured as mean diameter, from broadly 0.01 to 90% of the mean diameter of the particles and preferably from 10% to 90% of that diameter.

The art has described a number of magnetic particles which can be used in the assays of the invention. For example, U.S. Pat. Nos. 4,628,037, 4,695,392, 4,695,393, 4,698,302, 4,554,088, U.K. Pat. Application GB 2,005,019A and EP 0,180,384, describe a variety of magnetic particles which can be used with success. The particles may be paramagnetic or ferromagnetic and may be coated with various materials to which binding compounds are coupled so that the magnetic particle can be used in immunoassays. Desirably the magnetic particles used in the invention have a susceptibility of at least 0.001 cgs units and desirably the susceptibility is at least 0.01 cgs units. The magnetic particles may have a broad range of densities, i.e. from substantially less than that of water, 0.01, to 5 g/mL and preferably from 0.5 to 2 g/mL. The particle sizes can range from 0.001 to 100 $\mu$m and preferably from 0.01 to 10 $\mu$m. The concentration of the particles may range broadly from 1 to 10,000 $\mu$g per mL and preferably is from 5 to 1000 $\mu$g per mL.

Desirably the magnetic particles which are used have a low magnetic remanence, as described for example EP 0,180,384, so that after the magnetic field is removed from the collection zone, the particles demagnetize and can be swept out of the assay cell. Desirably the density, concentration and particle size of the magnetic particles is chosen such that the settling time is at least 0.5 mm/min and desirably it is above that rate.

Assays

A variety of assays can be performed using the methods of the invention.

Figure 2:
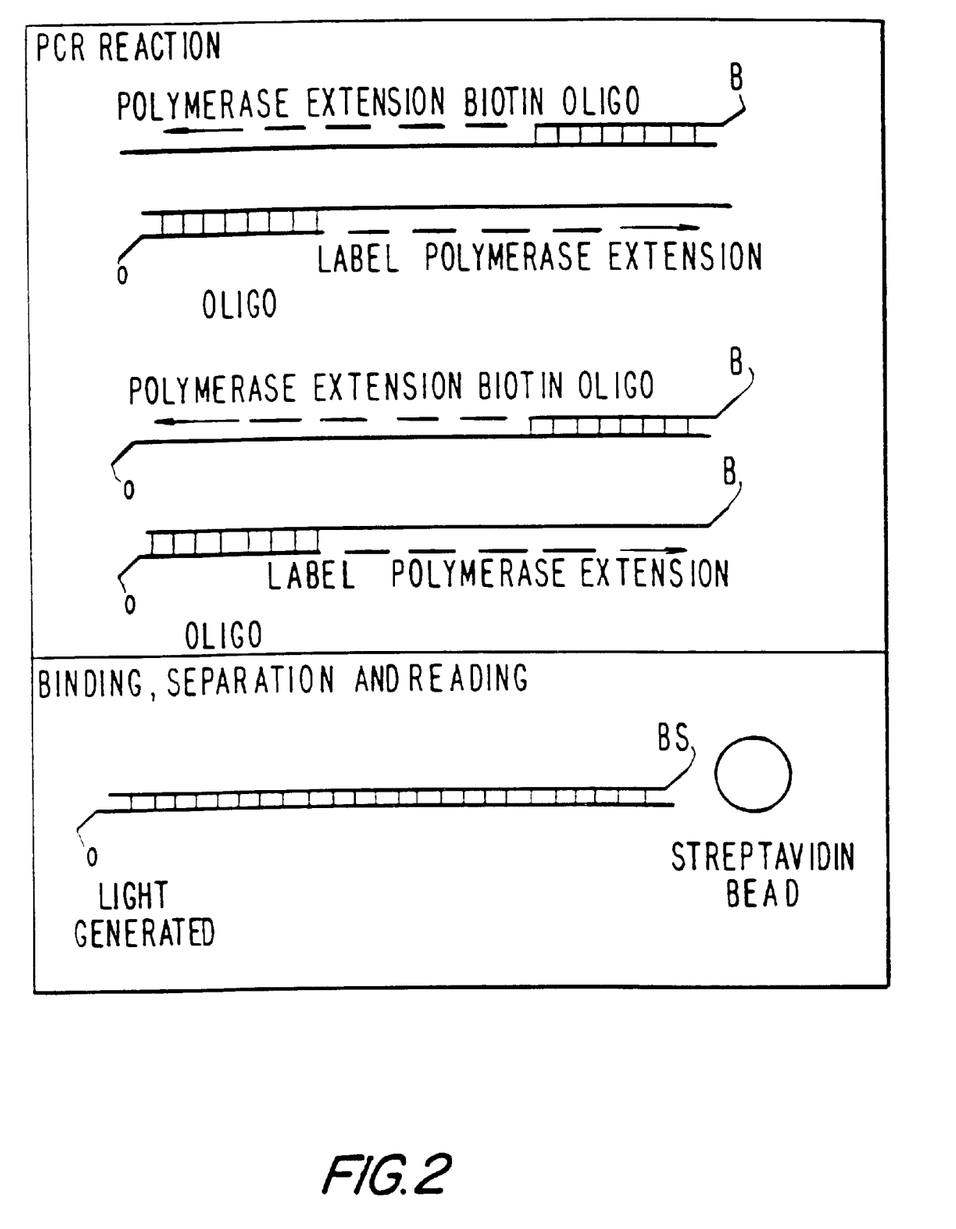
FIG. 2 is a schematic representation of a direct incorporation PCR format using chemiluminescent labeled oligonucleotides and biotin chemiluminescent labeled oligonucleotides as primers.

An assay is performed as shown in FIG. 2. The PCR products resulting from the reaction are labeled with biotin and a chemiluminescent label. Streptavidin beads capture the bifunctionalized DNA via biotin streptavidin binding and this is followed by washing. The bead bound product is then subjected to analysis detecting the chemiluminescent label.

Figure 3:
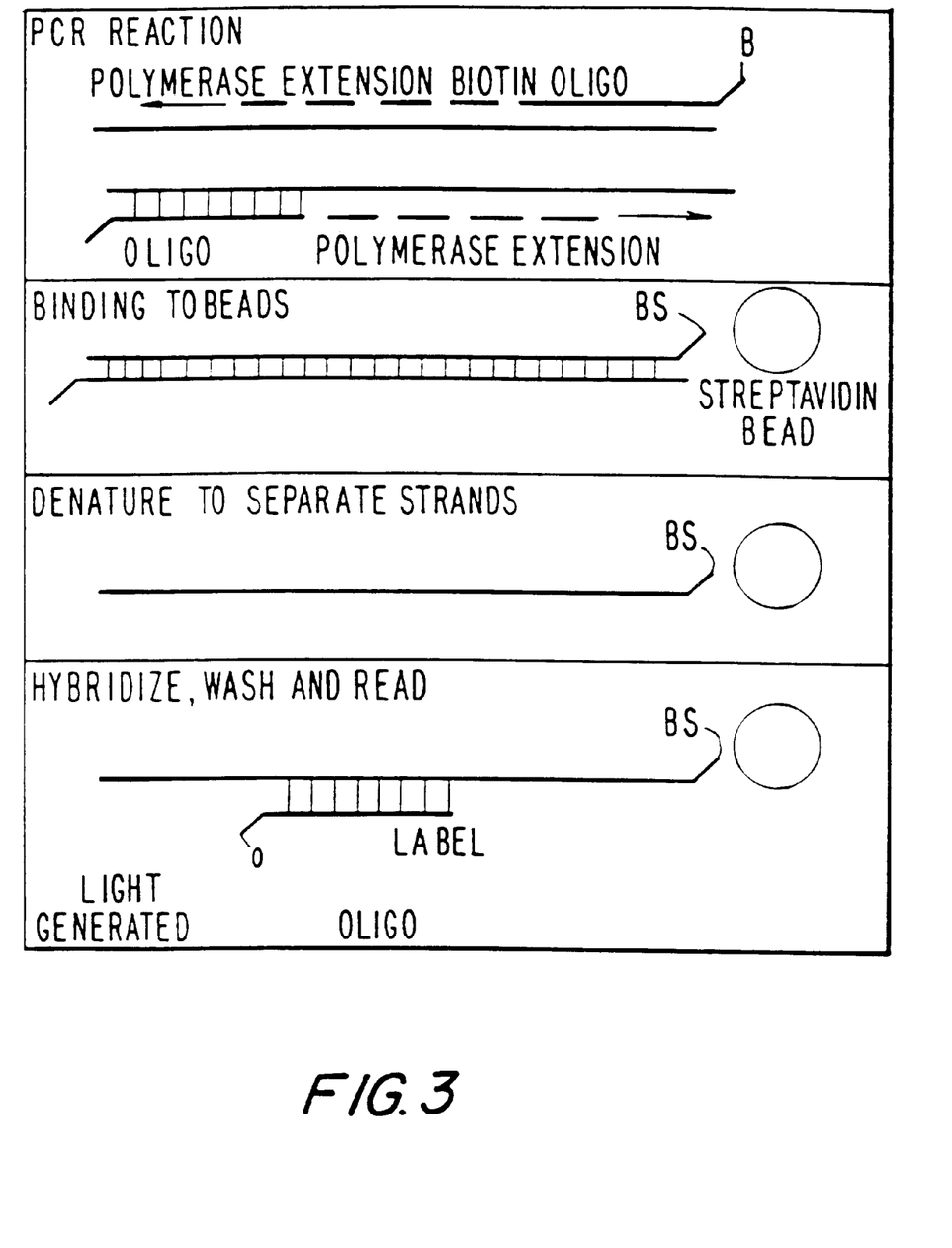
FIG. 3 is a schematic representation of a normal PCR format using a biotinylated primer to allow the generation of biotinylated PCR and PRODUCT.

An assay is performed as shown in FIG. 3. The biotinylated PCR product is captured on streptavidin beads and the non-biotinylated strand removed. The bead bound PCR product is then hybridized with a chemiluminescent labeled oligonucleotide. This is followed by chemiluminescent analysis to detect the label.

Figure 4:
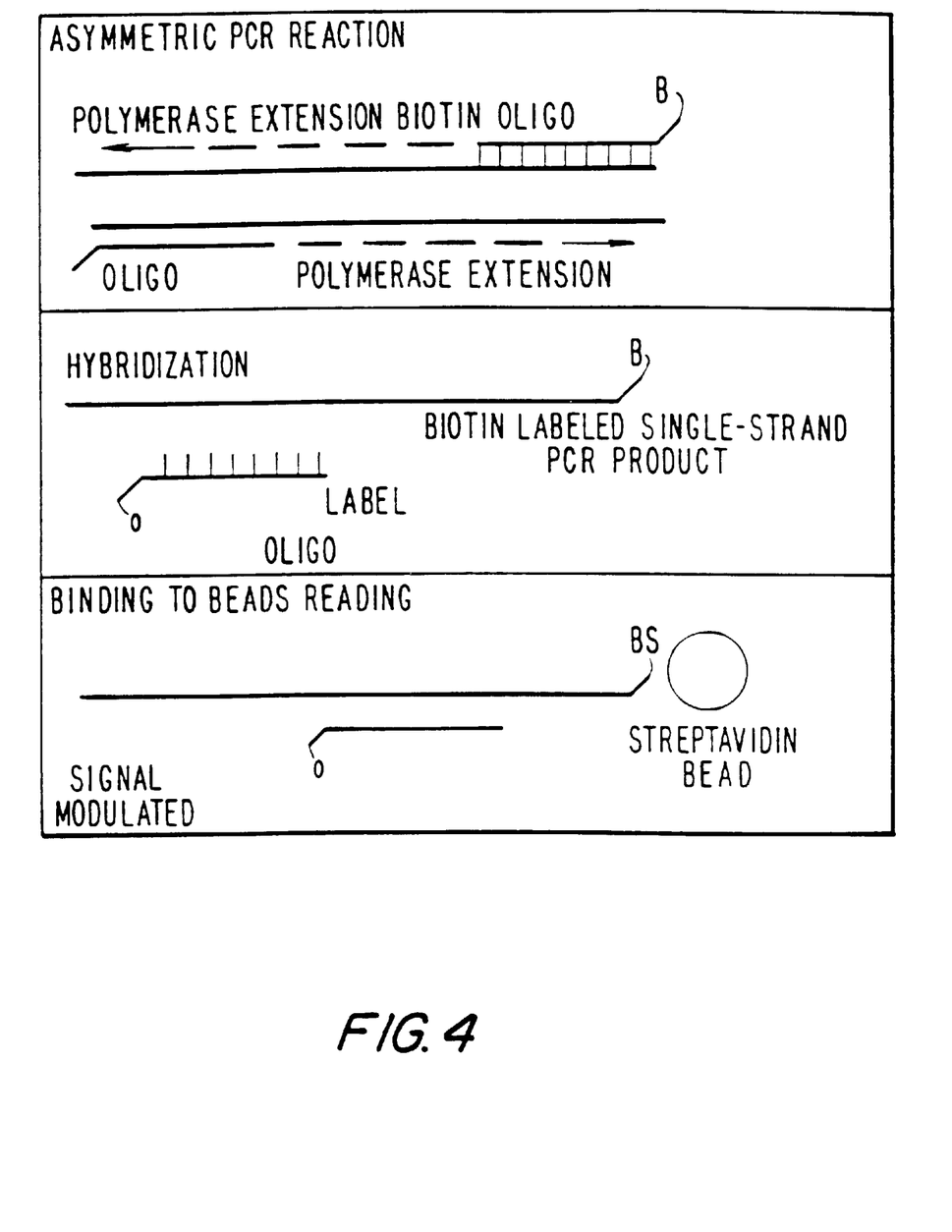
FIG. 4 is a schematic representation of an asymmetric PCR assay format generating single-stranded biotinylated DNA for later hybridization to chemiluminescent labeled oligonucleotides.

An assay is conducted as shown in FIG. 4. The hybrids are captured on streptavidin beads. This is followed by chemiluminescent analysis without washing.

EXAMPLES

Instrumentation, Materials, and Methods (1) Instrumentation

A flow-through apparatus as described in FIG. 1 was used.
Teflon Gasket (0.015" thick)
Plexiglas Faceplate
Inlet Tubing =0.042" id polypropylene
Aspiration Rates:variable from 0.01 to 5 mL/min
Luminometer using Hamamatsu R374 PMT (low gain red sensitive tube); PMT Voltage variable 0–1400 V

Example 1

Chemiluminescent Apparatus and Method for Deposition of Microparticles

Magnetic Collection using a Sedimentation Cell

Figure 5:
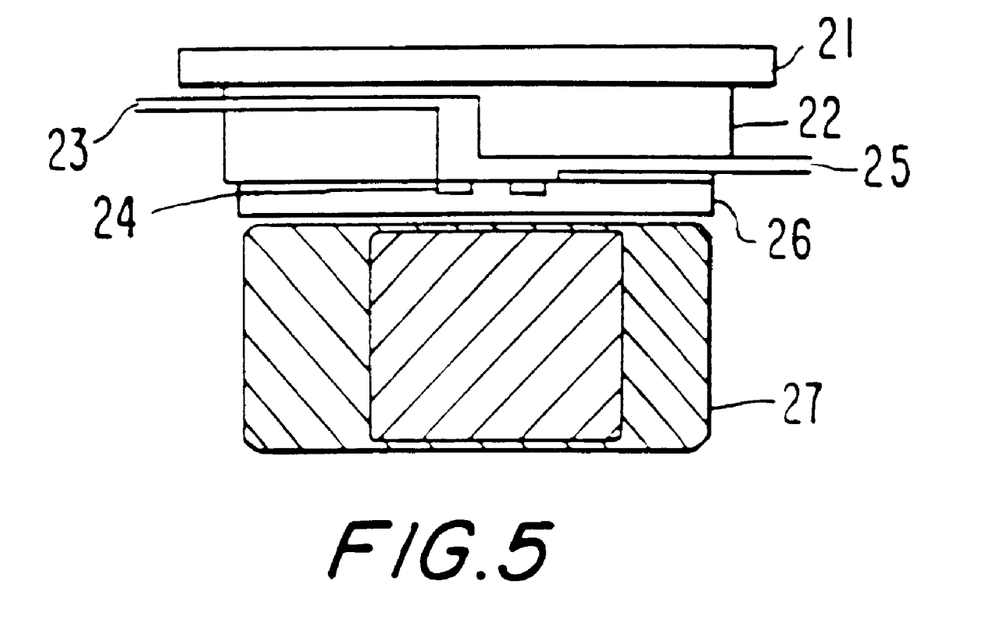
FIG. 5 is a schematic representation of a sedimentation assay cell which employs an electromagnet to cause the complex to settle in the collection zone surface.

A cell for conduct of an assay using magnetic force to cause the microparticulate to settle is shown in FIG. 5.

Reference numeral 21 refers to a transparent window, reference numeral 22 to a gasket, reference numeral 23 to the inlet in the cell block, reference numeral 25 to the sample outlet, reference numeral 26 to the cell block itself and reference 27 to an electromagnet.

The plane of the cell block is oriented horizontally. Labeled microparticles (Dynal) in buffer are drawn to the cell by means of a peristaltic pump. The pump is turned off after the microparticles reach the cell. The microparticles in the cell chamber are drawn to the collection zone by means of a magnetic field generated using electromagnet 27 operating at 12 volts and 1.5 amps. By application of the electromagnet, the rate of deposition of microparticles is greatly increased over that observed when the microparticles settle solely due to the force of gravity.

Example 2

Chemiluminescent Apparatus and Method for Deposition of Microparticles

Magnetic Collection using a Collection Cell

An assay is carried out in a cell as described in FIG. 1. With reference to FIG. 1, reference numeral 32 refers to transparent window, reference numeral 38 to a gasket, reference numeral 22 to an inlet in the cell block, reference numeral 20 to the cell block itself, reference numeral 24 to the sample outlet and reference numeral 37 to a permanent magnet.

The plane of the cell block is oriented horizontally. Labeled microparticles (Dynal) in buffer are drawn to the cell by means of a peristaltic pump 11. Prior to the sample introduction, permanent magnet 37 is positioned immediately below the collection zone at a distance of 0.035 inches. As the sample is being drawn to the cell, the microparticles collect in a collection zone, as defined by the area of the magnet. The pump is turned off. The longer the collection time, the more particles are collected.

Example 3

Use of Magnet for Deposition of Microparticles

Magnetic Field Orientation

Figures 6A, 6B:
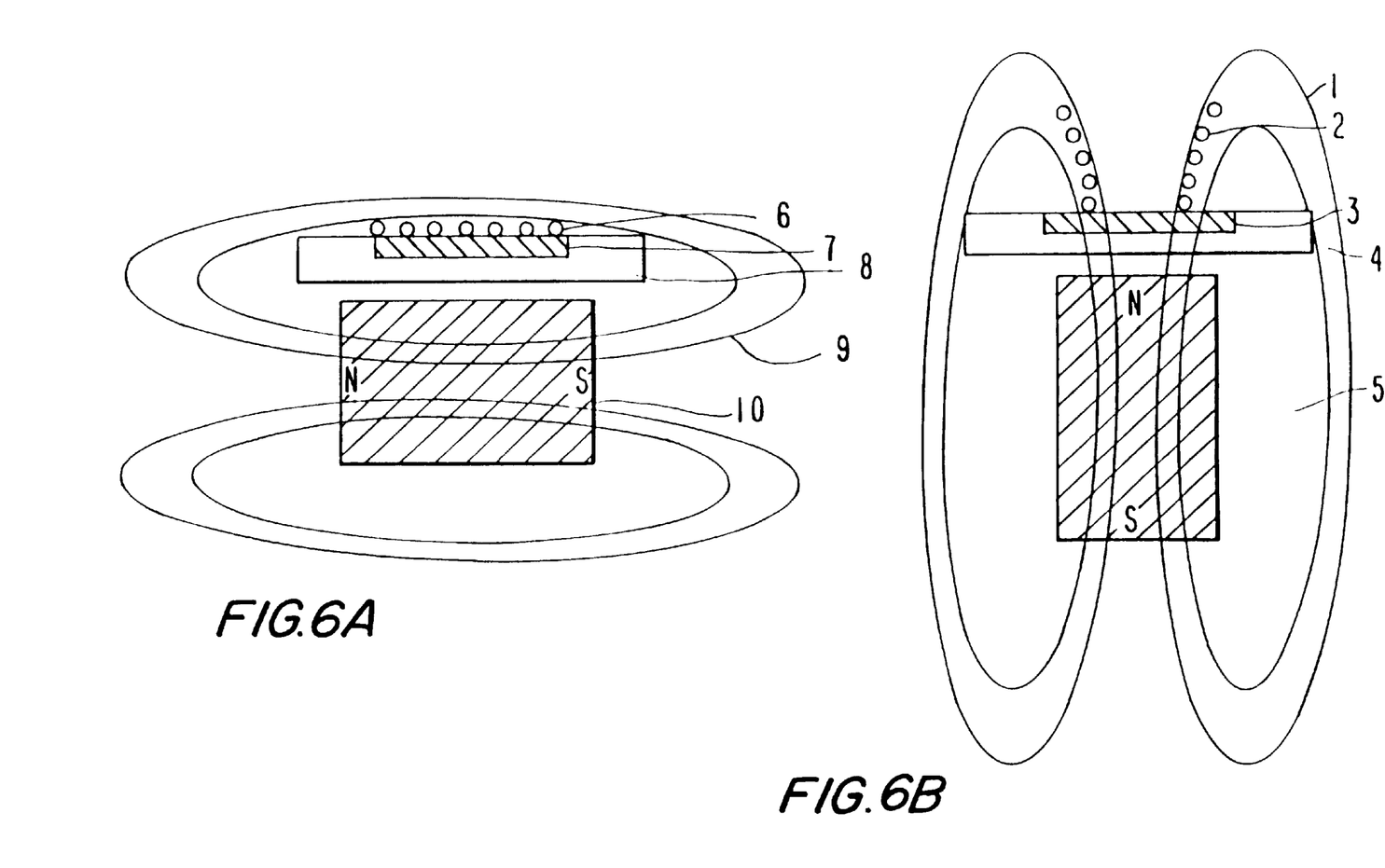
FIG. 6 is a schematic representation of the lines of force in the vicinity of the collection zone as a function of the orientation of the magnet beneath the surface of the collection zone.

Microparticles which are attracted to a magnet whether a permanent magnet or electromagnet, align with the orientation of the magnetic field. FIG. 6 depicts magnetic fields and the resultant particle arrangements which are parallel (A) and perpendicular (B) to the top surface of cell blocks 8 and 4, respectively, in the vicinity of that surface. One skilled in the art will appreciate that the orientation of the particles in the collection zone will affect the efficiency of subsequent contact with trigger.

Example 4

Particle Collection and Concentration by Filtration

Microparticles which are magnetically responsive, non-magnetically responsive, and of a wide range of densities can advantageously be collected by filtration upon the surface of a membrane filter. In one embodiment of the invention, the particles are pumped through a portion of a filter membrane which has pore sizes which are smaller than the diameter of the particles but preferably are substantially smaller than the particle diameter and at a sufficiently high surface density such that the collection of particles will not cause blockage of the pores. The collected particles are then exposed to trigger by pumping the trigger solution through the filter for the purpose of inducing chemiluminescence from the particles and measuring the luminescence to measure the quantity of chemiluminescent label on the particles.

In another embodiment, the membrane filter having pore sizes as described above is attached or placed upon the surface of an absorbent material such that capillarity or "wicking" will spontaneously draw fluids containing microparticles through the membrane filter without requiring any apparatus to induce the flow of fluid through the filter.

Such a filter is readily mounted in a flow cell such that the flow-path for the fluid is through the filter. Particles in the stream are trapped by the filter and are easily washed in-situ providing for a rapid and simple means for performing heterogeneous assays without any external washing apparatus.

Example 5

Particle Collection and Concentration by Centrifugal Method

Figure 7:
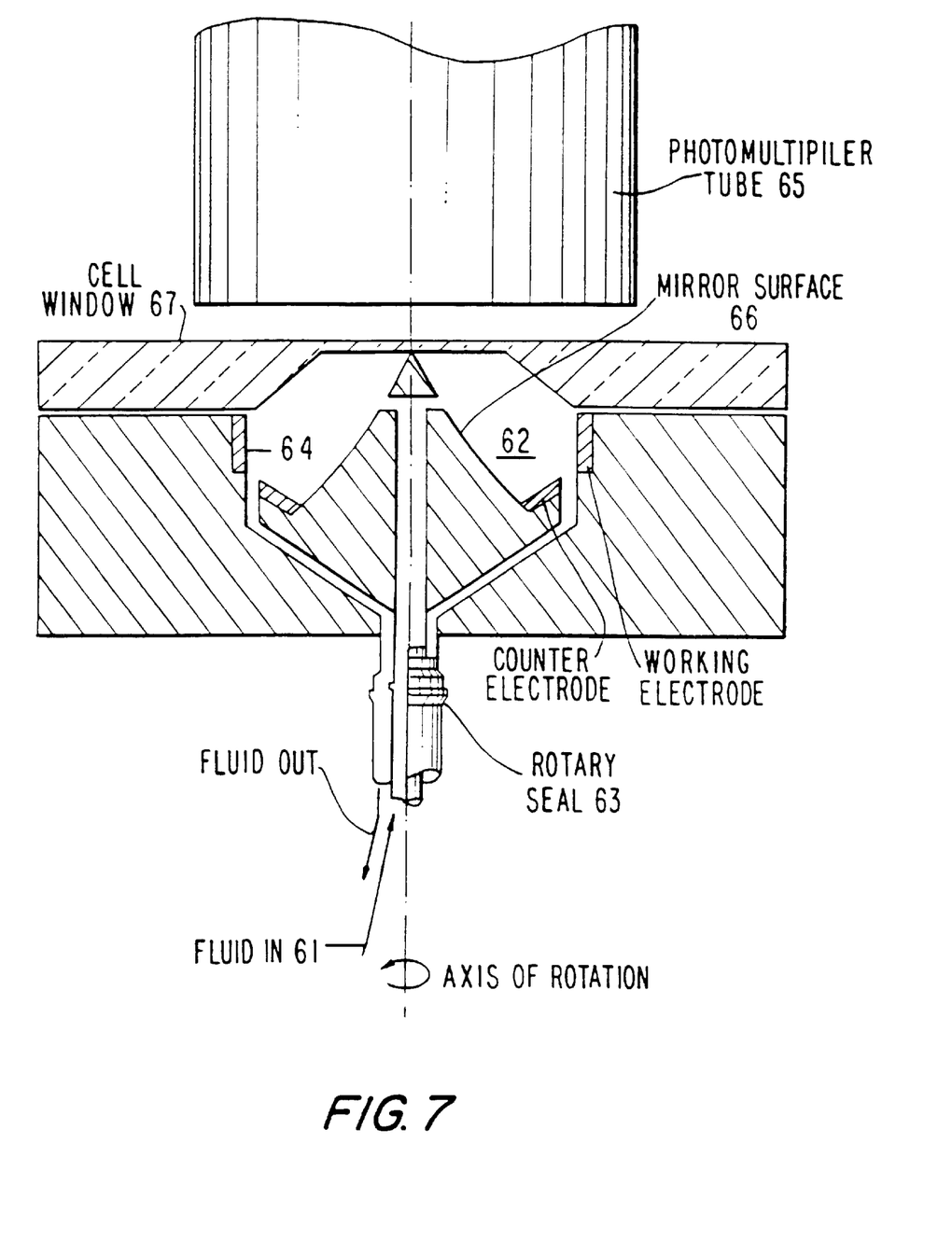
FIG. 7 is a schematic representation of a rotary flow cell wherein the complexes are deposited in the collection zone by centrifugation.

The rotary flow cell shown in FIG. 7 provides another means to collect the complex in order to measure luminescence. The assay solution 61 is pumped into cell 62 through rotary seal 63 while a rotational motion is imparted to the cell. The denser particles of the complex are concentrated in the collection zone. While the cell is still rotating the solution passes out of the cell. The light output passing through cell window 67 is measured by photomultiplier tube 65. The light output is directed from the collection zone and reflected off curved mirror surface 66 located at the center of the cell. The cell is then flushed and cleaned for the next cycle. This may be accomplished with the cell stopped or rotating.

Example 6

Coating of Particles With Labeled Non-specific Protein at Moderate Surface Concentration 30 mg (1 ml) of 4.5 um uncoated magnetically responsive, polystyrene M-450 DYNABEADS (DYNAL, Oslo, Norway) are washed by magnetic separation with a 150 mM phosphate buffer pH 7.5 solution using 2 ml/wash. 150 µg of acridinium ester-labeled antibody (London Diagnostics LumaTag TSH Labeled Antibody) in 1 ml of phosphate buffer saline (PBS) with 0.05% thimerosal is added to the particles. This mixture is allowed to incubate overnight at room temperature with agitation. The solution is then magnetically separated from the particles and the fluid removed. To block unreacted sites, 1 ml of 3% BSA/PBS with 0.05% sodium azide is added to the particles, and the resultant solution is allowed to incubate 2 hours at room temperature. The particles are washed 5 times (2 ml/wash), and then finally resuspended in 6 ml of the same buffer for storage.

Example 7

Chemiluminescent Measurement Using Magnetically Responsive Particles

Magnetically responsive particles (Dynal, Oslo, Norway) are coated with labeled proteins as described in Example 6. The coated particles are washed with phosphate buffer three times before making 2 mL of a 30 µg/mL suspension in 0.1 N $HNO_3$ and 0.5% hydrogen peroxide. Using a peristaltic pump, 500 ul of the particle suspension is drawn into the flow cell (Example 2). As the particles flow through the cell, they are attracted and concentrated into the collection zone by a magnet. After the particles are magnetically collected, a solution of 0.25 N NaOH, 0.5% hydrogen peroxide is drawn through the cell while the chemiluminescence is measured using a Hamamatsu R374 photomultiplier tube centered above the flow cell where particles have concentrated in the collection zone Example 8

Preparation of Physically Adsorbed Sheep Anti-Thyroid Stimulating Hormone (TSH) Coated Dynal Particles 1 mL of 4.5 μm uncoated magnetic, polystyrene particles with —OH residues on their surface (DYNAL, DYNA-BEADS M-450, DYNAL A.S. Oslo, Norway) is washed by magnetic separation with a 150 mM sodium carbonate/bicarbonate pH 9.6 solution using 2 mL/wash. 0.5 mg of purified monoclonal anti-TSH antibody (Catalog No. 5064031, Ventrex Laboratories, Inc., Portland, Me.) in 1 mL of the carb/bicarb solution is added to the particles. This mixture is incubated overnight at room temperature with mixing. The solution is then magnetically separated from the particles and removed. 1 mL of 3% BSA/PBS with 0.05% sodium azide is added and incubated 2 hours at room temperature with agitation to block unreacted sites. The particles are washed 5 times (2 mL/wash) and then finally resuspended in 1 mL of the same buffer for storage. The final concentration is 3% by weight.

Example 9

One Step Separation Sandwich Assay for Thyroid Stimulating Hormone (TSH)

100 μL serum calibrators (London Diagnostics TSH LumiTAG Kit), 25 μL LumaTag TSH acridinium ester-labeled antibody (London Diagnostics) in phosphate buffer and 25 μL anti-TSH-DYNAL particles (Example 8) in phosphate buffer are combined and incubated in polypropylene tubes for 15 minutes, at room temperature, with mixing. The particles are then washed by magnetic separation and then resuspended in 500 μL of pH 4, 10 mM carbonate/bicarbonate buffer. This wash procedure was repeated two additional times. The particles are drawn into a flow cell (Example 2), magnetically collected and a solution to trigger the chemiluminescent reaction is drawn through the flow cell (0.5% hydrogen peroxide, 0.25 N NaOH). The chemiluminescence for each sample is measured as described in Example 2. The chemiluminescent intensity is directly proportional to the concentration of analyte present in the sample (increasing intensity as the concentration of analyte increases).

Example 10

One Step Non Separation Sandwich Assay for Thyroid Stimulating Hormone (TSH)

100 μL serum calibrators (London Diagnostics TSH LumiTAG Kit), 25 μL LumaTag TSH acridinium ester-labeled antibody (London Diagnostics) in phosphate buffer and 25 μL anti-TSH-DYNAL particles (Example 8) in phosphate buffer are combined and incubated in polypropylene tubes for 15 minutes, at room temperature, with mixing. Prior to reading results, 1 mL of pH 4 100 mM carbonate/bicarbonate buffer is added. The particles are drawn into a flow cell (Example 2), magnetically collected and a solution to trigger the chemiluminescent reaction is drawn through the flow cell (0.5% hydrogen peroxide, 0.25 N NaOH). The chemiluminescence for each sample is read as described in Example 2. The chemiluminescent intensity is directly proportional to the concentration of analyte present in the sample (increasing intensity as the concentration of analyte increases).

Example 11

Chemiluminescent TSH Immunoassay Using Enzyme to Generate Trigger

Using magnetically responsive microparticles as the solid phase and acridinium ester as the label, a TSH immunoassay can be performed using the apparatus described in Example 2. An enzyme, glucose oxidase is used to convert a precursor of the trigger (glucose) to the trigger (hydrogen peroxide). The enzyme glucose oxidase catalyzes the oxidation of glucose to gluconic acid and hydrogen peroxide. Acridinium ester in the presence of hydrogen peroxide is oxidized to an excited state. The subsequent return to ground state of oxidized excited product results in the emission of light which is quantified. Magnetic microparticles coated with both specific antibody and enzyme glucose oxidase can be used (prepared as in Example 8 except that 0.5 mg of both antibody and enzyme (Sigma Chemical) are added to the particles for coating). Alternatively, separate particles coated with each reagent (antibody or enzyme) can be mixed and used in the assay (prepared separately as described in Example 8).

The TSH immunoassay is based on a two-site sandwich assay known in the art. Monoclonal anti-TSH antibody coated magnetic microparticles are prepared as described in Example 8. Enzyme glucose oxidase coated magnetic microparticles are prepared by the same method as antibody coated magnetic microparticles. Acridinium Ester labeled polyclonal anti-TSH antibody and the TSH standards are obtained from London Diagnostics. Enzyme substrate solution consists of 100 mM potassium phosphate buffer containing D-glucose (100 mg/ml).

A series of tubes (12×75 mm polypropylene ) are set up and labeled according to standards and samples to be assayed. Into each tube is added 100 μl of standard or sample or control, 100 μl of acridinium ester-labeled antibody and 100 μl of a mixture of anti-TSH antibody and enzyme coated microparticles. The tubes are incubated at room temperature with mixing for 15 min. Following incubation, 1 ml pH 4, 100 mM carbonate/bicarbonate buffer is added. The particles are drawn into a flow cell (Example 2), magnetically collected and the glucose substrate solution is drawn through the flow cell. The chemiluminescence for each sample is read as described in Example 2. The chemiluminescent intensity is directly proportional to the concentration of analyte present in the sample (increasing intensity as the concentration of analyte increases).

What is claimed is:

1. A method for performing a binding assay for an analyte of interest possibly present in a sample comprising:
  (a) forming a composition containing:
    (i) said sample;
    (ii) an assay-performance-substance comprising at least one compound selected from the group consisting of:
      (1) added analyte of interest or added analogue of said analyte;
      (2) a binding partner of said analyte or a binding partner of said analogue; and (3) a component capable of binding with (1) or (2); wherein said assay-performance-substance further contains a label compound linked to at least one of said (1), (2), and (3) and wherein said label compound is capable of chemiluminescing when triggered; and (iii) a plurality of particles capable of specifically binding with the analyte and/or said assay-performance-substance;

(b) incubating said composition to form a complex which includes a particle and said labeled component;

(c) introducing a suspension of said particles into a flow-cell;

(d) collecting said particles in a collection zone contained within said flow-cell thereby removing said particles from suspension, wherein said composition is flowed through the flow-cell at a sufficiently low rate of flow to permit collection of at least a portion of said particles;

(e) introducing into said collection zone a trigger capable of triggering said label such that said label chemiluminesces; and (f) measuring the emitted chemiluminescence from said label on said complex while said particles are collected at said collection zone to measure the presence of the analyte of interest in the sample.

2. A method as recited in claim 1 wherein said trigger is an oxidant capable of oxidizing said label.

3. A method as recited in claim 1 wherein said particles are magnetically responsive and said complex is magnetically collected in said collection zone.

4. A method as recited in claim 2 wherein said oxidant is hydrogen peroxide or superoxide.

5. A method as recited in claim 1 wherein said assay-performance-substance further contains an enzyme for converting a precursor to an oxidant capable of oxidizing said label, and said trigger is the precursor.

6. A method as recited in claim 5 wherein the enzyme is glucose oxidase, the precursor is glucose and the oxidant is hydrogen peroxide.

7. A method as recited in claim 1 wherein said particles further contain an enzyme for converting a precursor to an oxidant capable of oxidizing said label, and said trigger is the precursor.

8. A method as recited in claim 7 wherein the enzyme is glucose oxidase, the precursor is glucose and the oxidant is hydrogen peroxide.

9. A method as recited in claim 1 conducted as a batch process, the composition being permitted to reside within said cell for a time sufficient to permit collection of said particles.

10. A method as recited in claim 7 wherein said particles have a density of from 0.1 to 5 g/mL.

11. A method as recited in claim 10 wherein said particles have a density of from 0.5 to 2 g/mL.

12. A method as recited in claim 7 wherein the size of said particles, measured as the mean diameter, ranges from 0.001 to 100 $\mu$m.

13. A method as recited in claim 12 wherein the size of said particles ranges from 0.01 to 10 $\mu$m.

14. An assay method as recited in claim 7 wherein the concentration of particles in said composition is from 1 to 10,000 $\mu$g/mL.

15. A method as recited in claim 14 wherein said concentration of particles is in the range of from 5 to 1000 $\mu$g/mL.

16. A method as recited in claim 7 wherein said particles have a magnetic susceptibility of at least 0.001 cgs units.

17. A method as recited in claim 16 wherein the magnetic susceptibility is at least 0.01 cgs units.

18. A method as recited in claim 7 wherein the magnetic susceptibility, density, size and concentration of said particles in said composition is such that the settling rate of said particles is at least 0.5 mm/min.

19. A method as recited in claim 1, wherein said complex consists essentially of said analyte, said particle and said labeled component.

20. A method for performing a binding assay for an analyte of interest possibly present in a sample comprising:

(a) forming a composition containing:
  (i) said sample;
  (ii) an assay-performance-substance comprising at least one compound selected from the group consisting of:
    (1) added analyte of interest or added analogue of said analyte;
    (2) a binding partner of said analyte or a binding partner of said analogue; and
    (3) a component capable of binding with (1) or (2); wherein said assay-performance-substance further contains a label compound linked to at least one of said (1), (2), and (3) and wherein said label compound is capable of chemiluminescing when triggered; and
  (iii) a plurality of particles capable of specifically binding with the analyte and/or said assay-performance-substance;

(b) incubating said composition to form a complex which includes a particle and said labeled component;

(c) introducing a suspension of said particles into a cell;

(d) collecting said particles in a collection zone within said cell thereby removing said particles from suspension;

(e) introducing into said collection zone a trigger capable of triggering said label such that said label chemiluminesces; and (f) measuring the emitted chemiluminescence from said label on said complex while said particles are collected at said collection zone to measure the presence of the analyte of interest in the sample.

21. A method for performing a binding assay for an analyte of interest possibly present in a sample consisting essentially of:

(a) forming a composition containing:
  (i) said sample;
  (ii) an assay-performance-substance comprising at least one compound selected from the group consisting of:
    (1) added analyte of interest or added analogue of said analyte;
    (2) a binding partner of said analyte or a binding partner of said analogue; and
    (3) a component capable of binding with (1) or (2); wherein said assay-performance-substance further contains a label compound linked to at least one of said (1), (2), and (3) and wherein said label compound is capable of chemiluminescing when triggered; and
  (iii) a plurality of particles capable of specifically binding with the analyte and/or said assay-performance-substance;

(b) incubating said composition to form a complex which includes a particle and said labeled component;

(c) introducing a suspension of said particles into a cell;

(d) collecting said particles in a collection zone within said cell thereby removing said particles from suspension;

(e) introducing into said collection zone a trigger capable of triggering said label such that said label chemiluminesces; and (f) measuring the emitted chemiluminescence from said label on said complex while said particles are collected at said collection zone to measure the presence of the analyte of interest in the sample.

22. The method of claim 1, wherein said method does not involve separating said plurality of particles from free-label compound prior to introducing said suspension of particles into said flow-cell.

23. The method of claim 20, wherein said method does not involve separating said plurality of particles from free-label compound prior to introducing said suspension of particles into said cell.

24. The method of claim 1, wherein said collection zone comprises a magnet.

25. The method of claim 1, wherein said collection is performed magnetically.

26. The method of claim 20, wherein said collection zone is in a flow-through cell.

27. The method of claim 21, wherein said collection zone is in a flow-through cell.

28. A method for performing a binding assay for an analyte of interest possibly present in a sample consisting essentially of:

(a) forming a composition containing:
  (i) said sample;
  (ii) an assay-performance-substance comprising at least one compound selected from the group consisting of:
    (1) added analyte of interest or added analogue of said analyte;
    (2) a binding partner of said analyte or a binding partner of said analogue; and
    (3) a component capable of binding with (1) or (2); wherein said assay-performance-substance further contains a label compound linked to at least one of said (1), (2), and (3) and wherein said label compound is capable of chemiluminescing when triggered; and
  (iii) a plurality of particles capable of specifically binding with the analyte and/or said assay-performance-substance;

(b) incubating said composition to form a complex which includes a particle and said labeled component;

(c) introducing a suspension of said particles into a cell;

(d) collecting said particles in a collection zone within said cell thereby removing said particles from suspension;

(e) flowing a fluid through said cell thereby separating unbound components from said particles;

(f) introducing into said collection zone a trigger capable of triggering said label such that said label chemiluminesces; and (g) measuring the emitted chemiluminescence from said label on said complex while said particles are collected at said collection zone to measure the presence of the analyte of interest in the sample.

29. A method for performing a binding assay for an analyte of interest possibly present in a sample comprising:

(a) forming a suspension in a cell, said suspension containing:
  (i) said sample;
  (ii) an assay-performance-substance comprising at least one compound selected from the group consisting of:
    (1) added analyte of interest or added analogue of said analyte;
    (2) a binding partner of said analyte or a binding partner of said analogue; and
    (3) a component capable of binding with (1) or (2); wherein said assay-performance-substance further contains a label compound linked to at least one of said (1), (2), and (3) and wherein said label compound is capable of chemiluminescing when triggered; and
  (iii) a plurality of particles capable of specifically binding with the analyte and/or said assay-performance-substance;

(b) collecting said particles in a collection zone within said cell thereby removing said particles from suspension;

(c) flowing a fluid through said cell thereby separating unbound components from said particles;

(d) introducing into said collection zone a trigger capable of triggering said label such that said label chemiluminesces; and (e) measuring the emitted chemiluminescence from said label on said complex while said particles are collected at said collection zone to measure the presence of the analyte of interest in the sample.

30. A method for performing a binding assay for an analyte of interest possibly present in a sample consisting essentially of:

(a) forming a suspension in a cell, said suspension containing:
  (i) said sample;
  (ii) an assay-performance-substance comprising at least one compound selected from the group consisting of:
    (1) added analyte of interest or added analogue of said analyte;
    (2) a binding partner of said analyte or a binding partner of said analogue; and
    (3) a component capable of binding with (1) or (2); wherein said assay-performance-substance further contains a label compound linked to at least one of said (1), (2), and (3) and wherein said label compound is capable of chemiluminescing when triggered; and
  (iii) a plurality of particles capable of specifically binding with the analyte and/or said assay-performance-substance;

(b) collecting said particles in a collection zone within said cell thereby removing said particles from suspension;

(c) flowing a fluid through said cell thereby separating unbound components from said particles;

(d) introducing into said collection zone a trigger capable of triggering said label such that said label chemiluminesces; and (e) measuring the emitted chemiluminescence from said label on said complex while said particles are collected at said collection zone to measure the presence of the analyte of interest in the sample.

* * * * *